(12) United States Patent
Kana et al.

(10) Patent No.: US 6,221,035 B1
(45) Date of Patent: Apr. 24, 2001

(54) AUTOMATIC ANKLE CLAMP

(76) Inventors: Richard J. Kana, P.O. Box 452, Lexington, TX (US) 78947; Donald W. Dye, 803 Setting Sun Ct., Pflugerville, TX (US) 78660

( * ) Notice: Subject to any disclaimer, the term of this patent is extended or adjusted under 35 U.S.C. 154(b) by 0 days.

(21) Appl. No.: 09/193,074

(22) Filed: Nov. 16, 1998

(51) Int. Cl.[7] .............................. A61F 5/00; A61B 17/00
(52) U.S. Cl. .............................. 602/16; 602/27; 606/82; 606/88
(58) Field of Search .................. 606/80, 82, 86–90, 606/87, 96, 102, 177, 178, 62, 75, 79; 602/35, 36, 37, 38, 40, 27, 28, 29; 128/882

(56) References Cited

U.S. PATENT DOCUMENTS

| | | | |
|---|---|---|---|
| 2,089,993 | * | 8/1937 | Carabba . |
| 2,129,635 | * | 9/1938 | Anderson . |
| 5,002,547 | * | 3/1991 | Poggie et al. ................ 606/88 |
| 5,020,797 | * | 6/1991 | Burns ........................ 272/143 |
| 5,116,338 | * | 5/1992 | Poggie et al. ................ 606/90 |
| 5,197,944 | | 3/1993 | Steele ........................ 602/27 |
| 5,250,050 | * | 10/1993 | Poggie et al. ................ 606/79 |
| 5,578,039 | * | 11/1996 | Venderly et al. ............. 606/88 |
| 5,628,749 | * | 5/1997 | Venderly et al. ............. 606/80 |
| 5,628,750 | | 5/1997 | Whitlock .................... 606/88 |
| 5,643,272 | * | 7/1997 | Haines et al. ............... 606/80 |
| 5,667,511 | * | 9/1997 | Venderaly et al. ........... 606/88 |

OTHER PUBLICATIONS

Aaron A. Hofmann; Intermedics Orthopedics Inc., The Intermedics Natural Knee System With Cancellous–Structured Titanium, Surgical Technique; pp. 14–17.

Proteck Inc., Surgical Technique for the Wallaby Total Knee Prosthesis, Edition Jan. 1994, p. 12.

* cited by examiner

Primary Examiner—Kim M. Lee

(57) ABSTRACT

An automatic ankle clamp for use with an extramedullary alignment device includes a cradle having a triggering device movably mounted thereon. A pair of clamp arms are resiliently mounted for movement on the triggering device between an open position and a closed position. A latch device interconnects the clamp arms and the cradle for retaining the clamp arms in the open position and for simultaneously releasing the clamp arms to the closed position in response to movement of the triggering device relative to the cradle. The clamp is attachable to an extramedullary alignment device such that urging the cradle and triggering device into engagement with a patient's ankle, automatically and simultaneously releases the clamp arms to grip the patient's ankle. A base is mounted on the cradle for calibrated medial/lateral adjustment of the clamp relative to the extramedullary alignment device.

21 Claims, 5 Drawing Sheets

AUTOMATIC ANKLE CLAMP

BACKGROUND

The disclosures herein relate generally to total knee replacement and more particularly to an automatic clamp for an alignment guide used in resecting the tibial plateau.

During total knee surgery, the proximal portion of the tibia is cut away in preparation for a tibia implant. A cutting block or guide is typically used to aid the surgeon in locating and making the cut. Placement of the tibia cutting block is critical to establishing the plane of the tibial plateau for providing the proper alignment of the implant. One device commonly used for achieving property alignment is an extramedullary alignment assembly including an elongated rod. The distal end of the rod is connected to an ankle clamp used to stabilize the rod in order to assist in establishing the correct angle of cut for the tibial plateau.

Several known devices are used for this purpose. One such device includes a cradle that provides a "V" shaped notch for receiving the ankle. In this device the surgeon or an assistant must hold the ankle cradle in place during alignment.

In another known device, a "V" shaped cradle is held in place by a strap or a tension spring which wraps around the ankle and fastens to the cradle. This device securely holds the clamp in place after alignment is established. However, two hands are required to position the device during alignment.

U.S. Pat. No. 5,628,750 discloses a tibial resection guide alignment device including an extramedullary mount having a separate extramedullary member which may be removably mounted to a base member. A bottom assembly is connected to the extramedullary member by which the device may be connected around a patient's lower leg or ankle. A "V" shaped cradle includes two spring loaded arms that close around the ankle for stability and require the use of two hands for operation.

In U.S. Pat. No. 5,197,944, an ankle clamp apparatus for use in tibial cutting instruments has a frame with pivoting arms attached for gripping a patient's ankle during use. The arms can be held open with latches prior to placement and quickly released to grip the patient's leg by depressing the latches. A "V" shaped cradle includes spring loaded arms. The arms may be locked in an open position and released to a closed position in response to depressing an individual button for each arm. Although this device purports to be for single handed operation, it requires each button to be separately depressed for releasing a respective arm. Therefore, in order to release both arms simultaneously, both buttons must be depressed simultaneously, which requires two handed operation.

Single handed use is very desirable during surgery. A probable limitation with the individual buttons for releasing the arms is the inability to simultaneously reach both buttons with the same hand that is positioning the clamp, therefore negating the single handed use. Another problem might be the accidental misalignment of the clamp. When only one arm closes from one side, the cradle may shift to the opposite side that is not yet being held. Again, this may require the use of a second hand to maintain alignment during clamping.

Therefore, what is needed is a clamping device which attaches to the alignment rod and which automatically clamps onto the patient's ankle when engaged therewith such that the surgeon's hands remain free to stabilize the extramedullary alignment assembly and cutting block.

SUMMARY

One embodiment, accordingly, provides a clamp that may be locked in an open or cocked position which holds spring loaded arms ready to automatically and simultaneously release and clamp onto the ankle after alignment is accomplished. To this end, an automatic clamp includes a cradle having a first part and a second part movable relative to the first part. A pair of clamp arms are resiliently mounted for movement on the cradle between an open position and a closed position. A latch device interconnects the clamp arms and the cradle for releasing the clamp arms for movement from the open position to the closed position in response to the second part moving relative to the first part.

A principal advantage of this embodiment is that the clamp arms may be set in an open position. Using one hand the surgeon may align the clamp. Once alignment is made, merely pushing the "V" cradle including a triggering device against the distal tibia will release both arms to lock the instrument in place. Both arms will close simultaneously, not allowing the cradle to shift in either direction. No shifting of the hand or reaching with fingers to push buttons is required, thus allowing a true, one handed operation.

BRIEF DESCRIPTION OF THE DRAWING FIGURES

DETAILED DESCRIPTION

Figure 1:
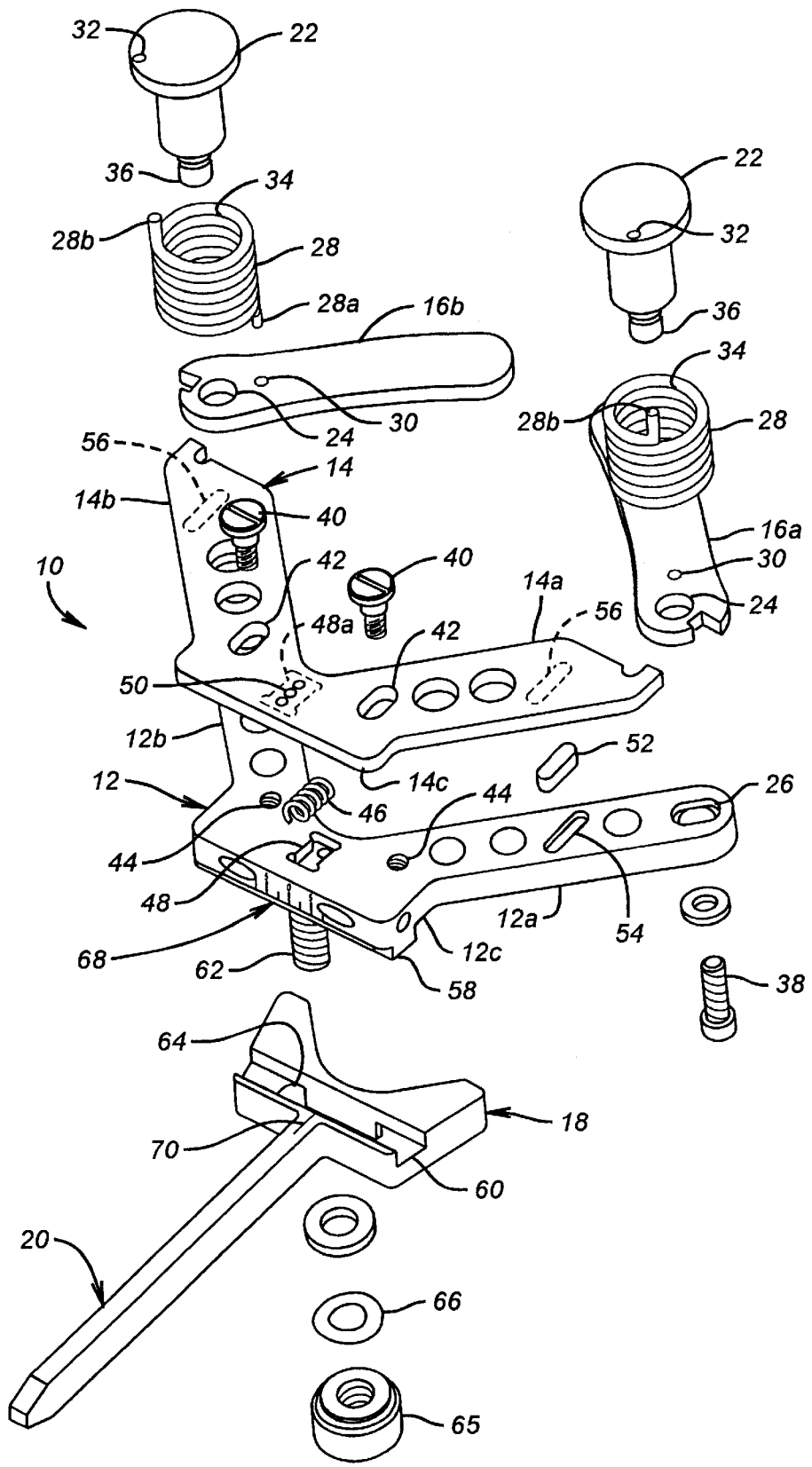
FIG. 1 is an exploded view illustrating an embodiment of an automatic clamp device.

An automatic clamp device is generally designated 10 in FIG. 1, and is provided for use with an extramedullary alignment device for one-handed operation in securing the device onto a patient's ankle. Clamp device 10 includes a cradle 12 including a first side 12a and a second side 12b, each joined at a main portion 12c. A triggering device 14 is provided to be movably mounted on cradle 12 and includes a first side 14a and a second side 14b, also joined at a main portion 14c. A first clamp arm 16a is provided for pivotal movement on first side 12a of cradle 12 and is engaged with an end of first side 14a of triggering device 14. Similarly, a second clamp arm 16b is provided for pivotal movement on second side 12b of cradle 12 and is engaged with an end of second side 14b of triggering device 14. A base 18 is mounted on cradle 12 for calibrated adjustment therewith. An extension 20 is provided on base 18 for adjustably attaching the cradle 12 to an extramedullary alignment device (to be discussed below).

A respective mandrel 22 is used to mount each clamp arm 16a, 16b on cradle 12. This is accomplished by mounting the arms 16a, 16b on a respective side 12a, 12b of cradle 12, so that an opening 24 of each clamp arm 16a, 16b is aligned with an opening 26 of each respective side 12a, 12b of cradle 12. Also, a respective torsion spring 28 has a first end 28a engaged in an opening 30 in each clamp arm 16a, 16b, and a second end 28b engaged in an opening 32 in each mandrel 22. Each mandrel 22 is seated in an opening 34 in a respective one of the torsion springs 28 such that an end 36 of each mandrel 22 extends into opening 24 in a respective one of the clamp arms 16a, 16b. A respective fastener 38 extends through each opening 26 of sides 12a, 12b to engage the end 36 of each mandrel 22.

Triggering device 14 is mounted for reciprocal movement on cradle 12 by means of a pair of fasteners 40, each of which extend through a respective slot 42 formed in triggering device 14, and are received in a respective threaded opening 44 formed in cradle 12. A portion of a spring 46 is compressed in a slot 48 formed in cradle 12 and another portion of the spring is also compressed in a similar slot 48a formed in triggering device 14. Slots 48 and 48a are of the same size but are slightly offset so as to normally position triggering device 14 offset from cradle 12 toward clamp arms 16a, 16b. A plurality of seep holes 50 are provided in triggering device 14 in communication with slot 48a for providing access to clean any debris accumulated around the spring 46. Movement of triggering device 14 relative to cradle 12 is guided by a pair of guide tabs 52, only one of which is visible in FIG. 1. One of the guide tabs 52 is mounted in a slot 54 in side 12a of cradle 12 and another tab is mounted in a slot in side 12b (not visible in FIG. 1). Tabs 52 also seat in a pair of similar slots 56 formed in sides 14a and 14b of triggering device 14 and aligned with slots 54.

Cradle 12 includes a key 58 which is movably mounted in the keyway 60 formed in base 18. A threaded fastener 62 extends through an elongated slot 64 formed in keyway 60. Fastener 62 is received and retained in a movable friction connection with base 18 by means of a threaded receiver 65 and a spring washer 66, so that medial/lateral adjustment of cradle 12 may be made relative to base 18. The adjustment is calibrated by varying alignment between a scale 68 on cradle 12 and a reference 70 on base 18.

Figure 2:
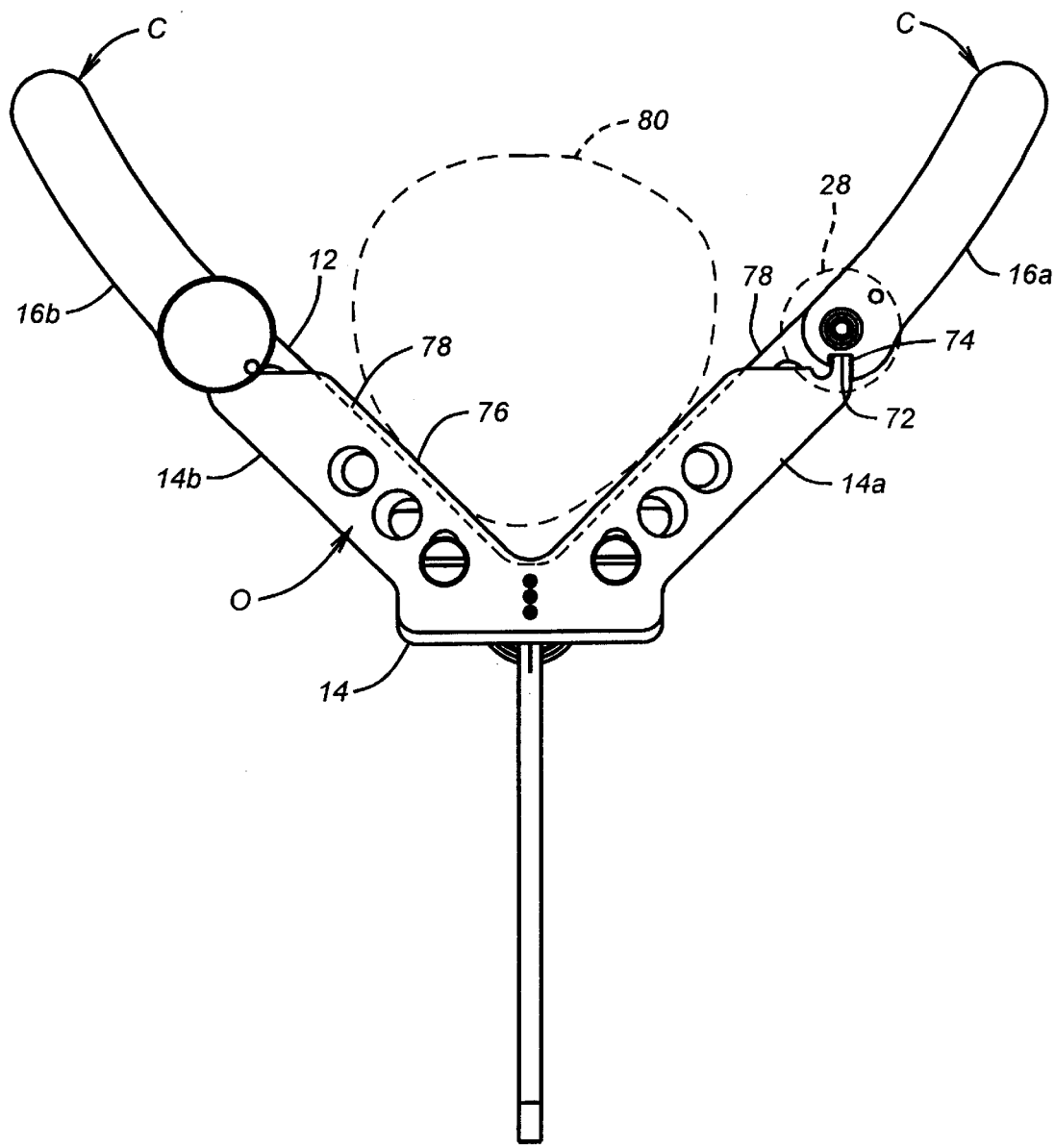
FIG. 2 is a top view illustrating an embodiment of the clamp device in a cocked position.
Figure 2A:
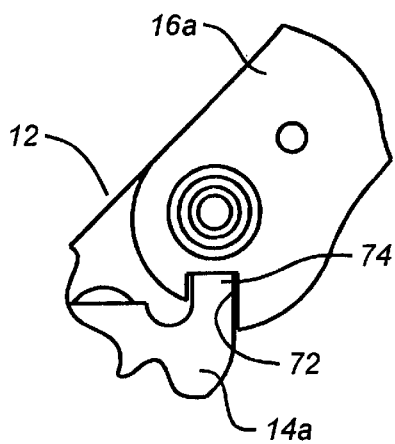
FIG. 2a is a partial top view illustrating an embodiment of an engaged triggering device.

In operation, clamp arms 16a, 16b, FIG. 2 each include a notch 72 on a distal end thereof. A mating tab 74 extends from a distal end of sides 14a, 14b for engagement with notches 72. The torsion springs 28 which resiliently mount clamp arms 16a, 16b on cradle 12, described above, permit clamp arms 16a, 16b to be cocked into a first or open position C wherein notches 72 engage with tabs 74, FIG. 2a. Also, triggering device 14 is urged into an offset position O, relative to cradle 12 such that a movable trigger edge 76 of triggering device 14 overhangs a stationary edge 78 of cradle 12 due to a force imposed by compressed spring 46, discussed above, which also urges tabs 74 into notches 72.

Figure 3:
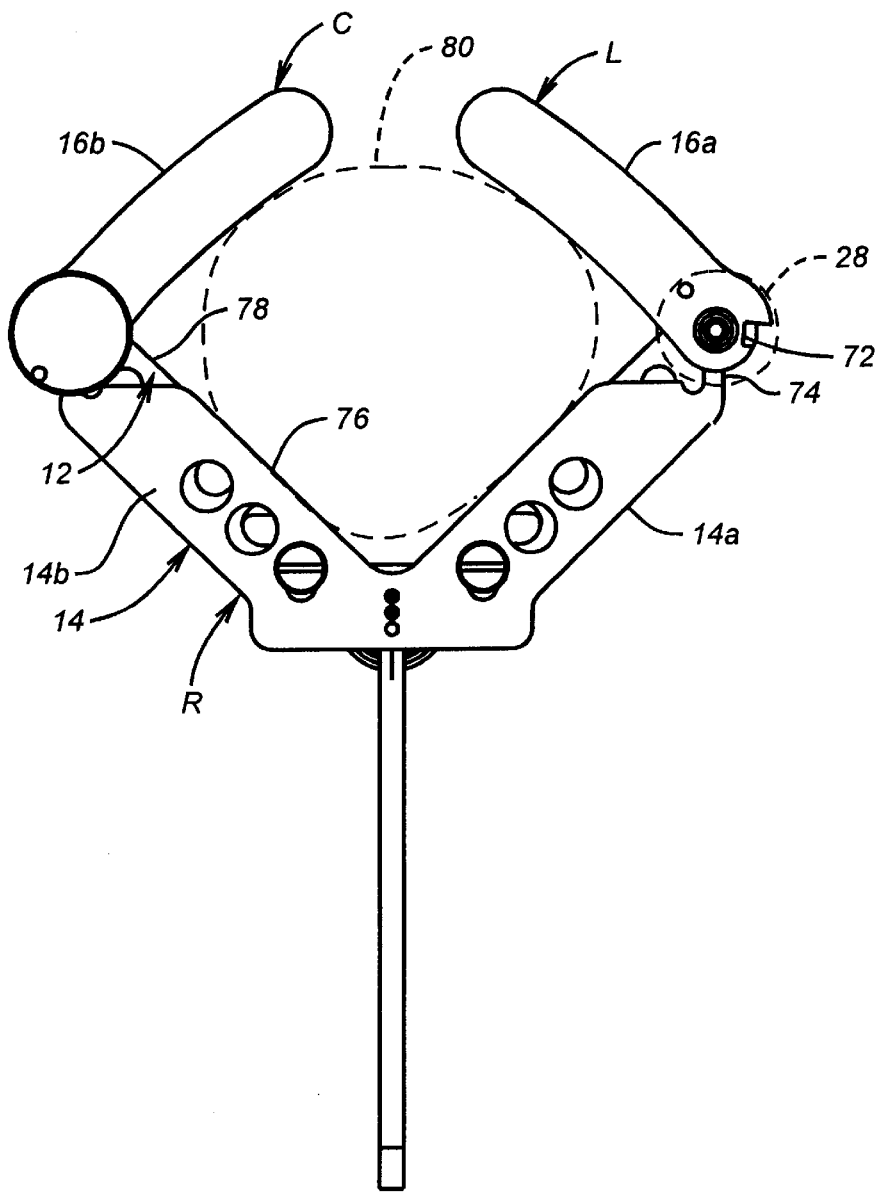
FIG. 3 is a top view illustrating an embodiment of the clamp device in a clamped position.
Figure 3A:
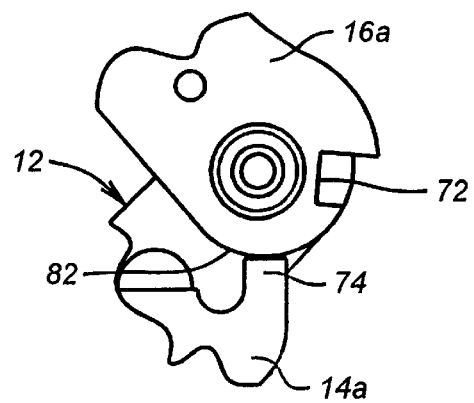
FIG. 3a is a partial top view illustrating an embodiment of a released triggering device.
Figure 4:
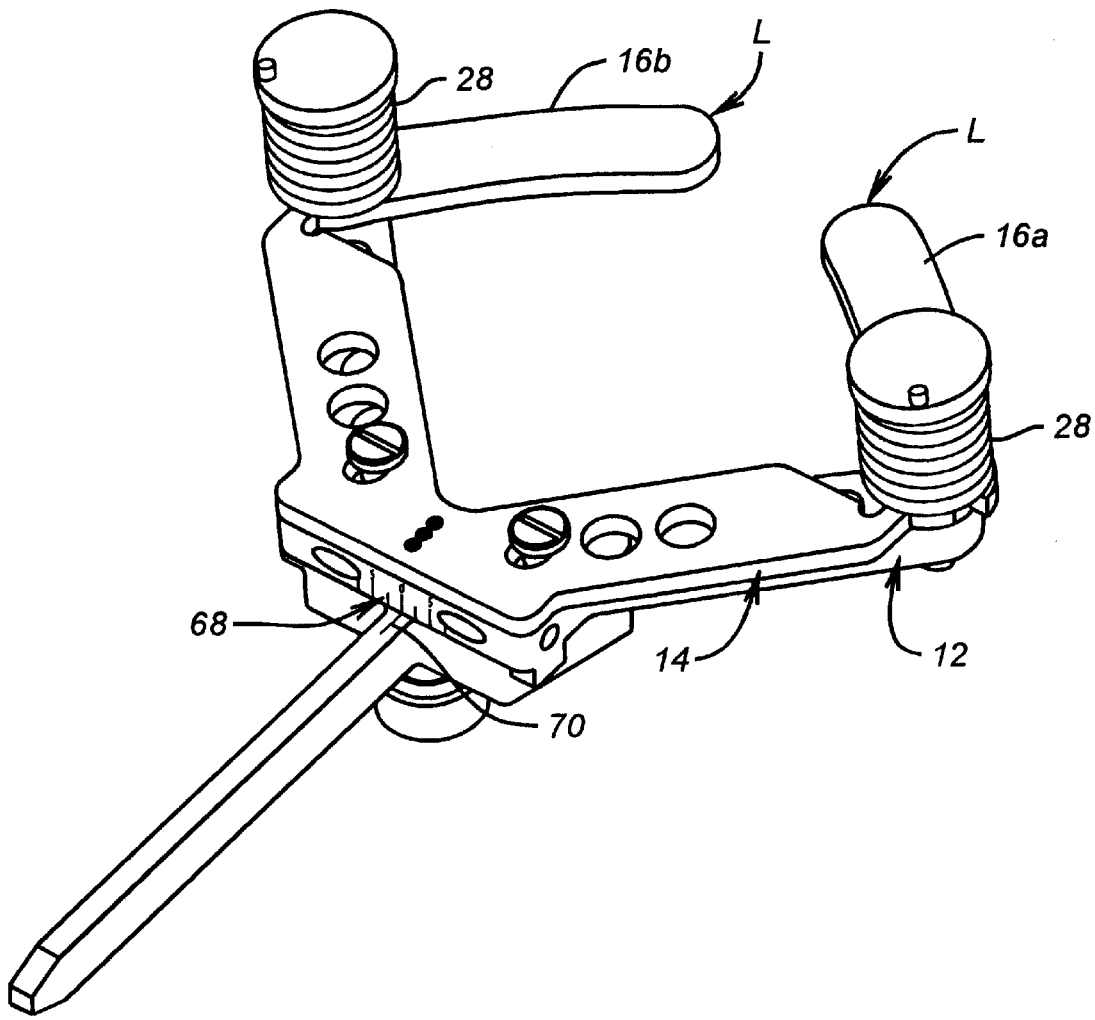
FIG. 4 is an isometric view illustrating an embodiment of the clamp device in the clamped position.

Forced engagement of trigger edge 76 with a patient's lower leg or ankle region 80, moves triggering device 14 relative to cradle 12 to a released position R, FIG. 3, such that movable trigger edge 76 of triggering device 14 is substantially aligned with stationary edge 78 of cradle 12. This movement is sufficient to move tabs 74 out of engagement with notches 72, which permits forces imposed by torsion springs 28 to rotate clamp arms 16a, 16b to a second or clamped position L, see also FIGS. 3a and FIG. 4. The force imposed by compressed spring 46 maintains tabs 74 engaged with an articulating surface 82 of clamp arms 16a, 16b, see FIG. 3a. As a result, when clamp arms 16a, 16b are returned to the cocked open position C, FIG. 2, tabs 74 are urged into notches 72.

Figure 5:
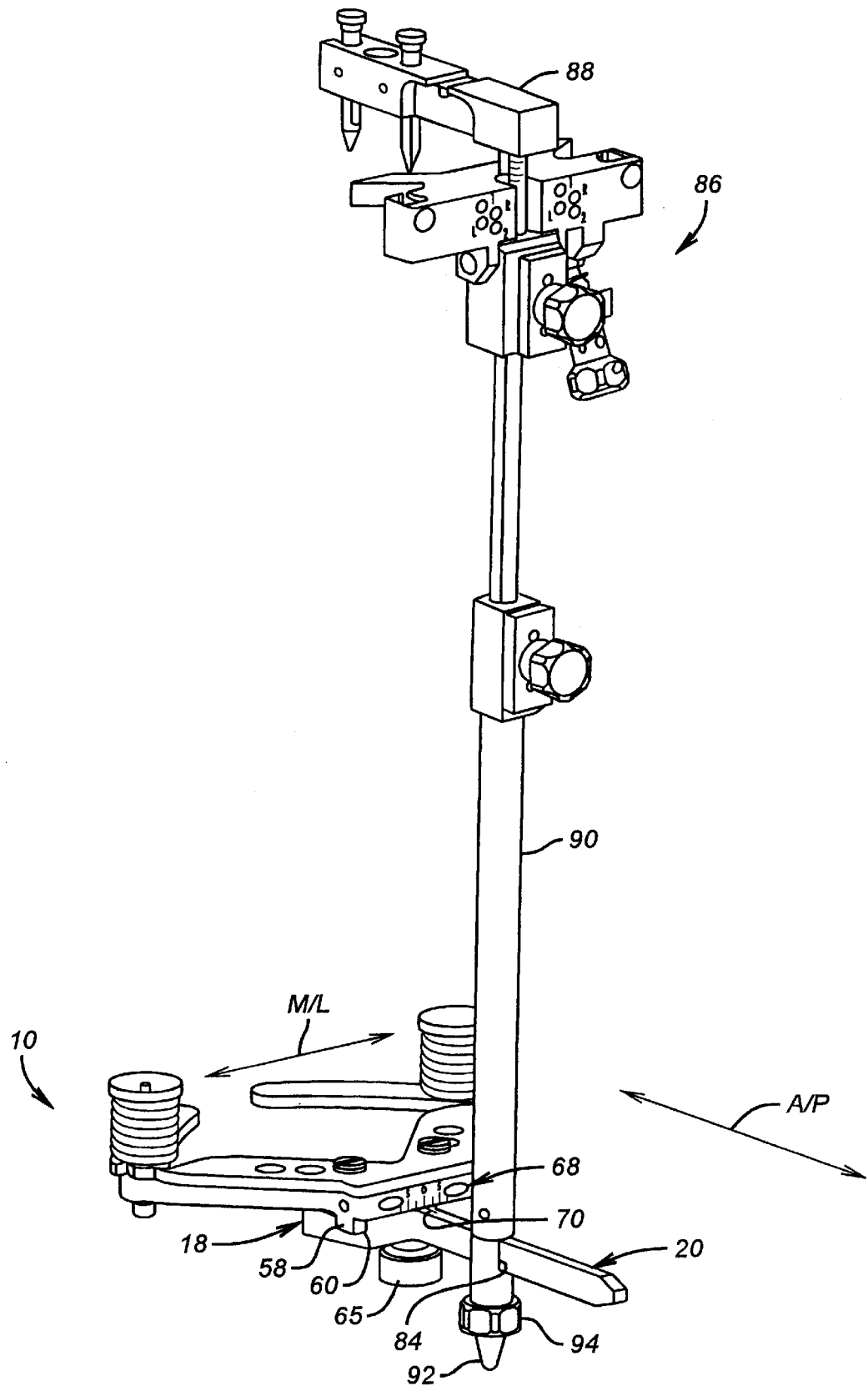
FIG. 5 is an isometric view illustrating an embodiment of the clamp device attached to an extramedullary alignment device.

Extension 20 of base 18 is inserted into a slot 84 of an extramedullary alignment device 86, FIG. 5. A first end 88 of extramedullary device 86 is appropriately attached to a patient's knee, not shown, in a manner which is well known. An alignment rod 90 extends to a second end 92 of extramedullary device 86. Clamp 10 is attached to second end 92 by insertion of extension 20 into slot 84. An adjustment member 94 at second end 92 permits anterior/posterior adjustment of clamp 10 via extension 20 within slot 84, in the directions indicated by directional arrow A/P. Threaded receiver 65 may be manipulated to permit medial/lateral adjustment of clamp 10 via movement of key 58 in keyway 60 for calibrated adjustments measured by scale 68 and reference 70, in the directions indicated by directional arrow M/L.

As a result, one embodiment provides an automatic clamp including a cradle having a first part and a second part movable relative to the first part. A pair of clamp arms are resiliently mounted for movement on the cradle between an open position and a closed position. A latch device interconnects the clamp arms and the cradle for releasing the clamp arms for movement from the open position to the closed position in response to the second part moving relative to the first part.

Another embodiment provides an automatic clamp including a cradle and a triggering device movably mounted on the cradle. A pair of clamp arms are resiliently mounted for movement on the triggering device between an open position and a closed position. A latch device interconnects the clamp arms and the cradle for releasing the clamp arms for movement from the open position to the closed position in response to movement of the triggering device relative to the cradle.

Another embodiment provides an automatic ankle clamp for use with an extramedullary alignment device including a cradle having a first part and a second part. A cradle includes a trigger movably mounted thereon. A pair of clamp arms are resiliently mounted for movement on the cradle between an open position and a closed position. A latch device interconnects the clamp arms and the trigger for simultaneously releasing the clamp arms for movement from the open position to the closed position in response to the trigger being moved relative to the cradle. An extension is provided for adjustably attaching the cradle to the alignment device.

Another embodiment provides an automatic gripping clamp including a cradle and a trigger movably mounted thereon. A pair of clamp arms are resiliently mounted for movement on the cradle between an open position and a closed position. A latch device interconnects the clamp arms and the trigger for retaining the clamp arms in the open position and for simultaneously releasing the clamp arms to the closed position in response to movement of the trigger relative to the cradle. A base is mounted on the cradle for calibrated adjustment of the cradle.

A further embodiment provides a method of securing an alignment device on a patient's ankle. A triggering device is movably mounted on a cradle. A pair of clamp arms are resiliently mounted on the triggering device for movement between an open position and a closed position. The clamp arms and the cradle are interconnected with a latch device for retaining the clamp arms in the open position and for releasing the clamp arms to the closed position. The cradle is attached to an extramedullary alignment device. The latch device is engaged for resiliently loading the clamp arms in the open position. The cradle and triggering device are urged into engagement with the patient's ankle for automatically and simultaneously releasing the clamp arms to grip to patient's ankle.

As it can be seen, the principal advantages of these embodiments are that the clamp may be locked open or cocked by an assistant or by the surgeon at the time of use. Cocking the clamp holds the two spring loaded arms in the open position. Using one hand the surgeon may align the clamp. Once alignment is made, merely pushing the "V" shaped cradle including the triggering device against the distal tibia adjacent the ankle will release both arms to lock the instrument in place. Both arms will close simultaneously, not allowing the cradle to shift in either direction. No shifting of the hand or reaching with fingers to push buttons is required, thus allowing a true, one handed operation.

Additionally, the surgeon may shift the distal tip of the extramedullary rod in either the medial or lateral direction by sliding the medial/lateral adjustment on the ankle clamp. The slide is held in place by spring tension or may be securely locked in place with a finger knob. To further aid the surgeons ability to obtain the proper slope for the bone resection, the distal tip of the extramedullary rod may also be shifted in the anterior or posterior direction. Adjustment is accomplished by sliding the extramedullary rod to the desired position on the ankle clamp.

Although illustrative embodiments have been shown and described, a wide range of modifications, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. An automatic clamp comprising:
   a cradle including a first part and a second part movable relative to the first part;
   a pair of clamp arms resiliently and pivotally mounted for movement on the cradle between an open position and a closed position;
   a trigger member movably mounted on the cradle and having a first end engaged with a first one of the clamp arms and a second end engaged with a second one of the clamp arms; and
   a latch device interconnecting the clamp arms and the cradle for releasing the clamp arms for movement from the open position to the closed position in response to the second part moving relative to the first part.

2. The clamp as defined in claim 1 wherein each end of the trigger member includes a tab and each clamp arm includes a notch for receiving a respective one of the tabs.

3. The clamp as defined in claim 1 further comprising an extension adjustably mounted on the cradle for medial/lateral adjustment.

4. The clamp as defined in claim 3 further comprising a scale on the cradle for gauging the medial/lateral adjustment.

5. A clamp comprising:
   a cradle;
   a triggering device movably mounted on the cradle;
   a pair of clamp arms resiliently mounted for movement on the triggering device between an open position and a closed position; and
   a latch device interconnecting the clamp arms and the cradle for releasing the clamp arms for movement from the open position to the closed position in response to movement of the triggering device relative to the cradle.

6. The clamp as defined in claim 5 wherein the clamp arms are pivotally mounted on the cradle.

7. The clamp as defined in claim 6 wherein the triggering device includes a first end engaged with a first one of the clamp arms and a second end engaged with a second one of the clamp arms.

8. The clamp as defined in claim 7 wherein the triggering member and each clamp arm include a releasable latch connection responsive to movement of the triggering device on the cradle.

9. The clamp as defined in claim 5 further comprising an extension adjustably mounted on the cradle for medial/lateral adjustment.

10. The clamp as defined in claim 9 further comprising a scale on the cradle for gauging the medial/lateral adjustment.

11. The clamp as defined in claim 5 further comprising means for guiding movement of the triggering device on the cradle.

12. The clamp as defined in claim 11 further comprising resilient means engaging the cradle and triggering device for urging the triggering device toward the clamp arms.

13. An automatic ankle clamp for use with an extramedullary alignment device comprising:
   a cradle including a trigger movably mounted thereon;
   a pair of clamp arms resiliently mounted for movement on the cradle between an open position and a closed position;
   a latch device interconnecting the clamp arms and the trigger for simultaneously releasing the clamp arms for movement from the open position to the closed position in response to the trigger being moved relative to the cradle; and
   an extension for adjustably attaching the cradle to the alignment device.

14. The ankle clamp as defined in claim 13 wherein the extension is adjustably mounted on the cradle for medial/lateral adjustment.

15. The ankle clamp as defined in claim 14 further comprising a scale on the cradle for gauging the medial/lateral adjustment.

16. The ankle clamp as defined in claim 13 further comprising a guide extending between the cradle and the trigger for guiding movement of the trigger on the cradle.

17. The clamp as defined in claim 16 wherein the trigger is resiliently engaged with the cradle for urging the trigger into engagement with the clamp arms.

18. An automatic gripping clamp comprising:
   a cradle;
   a trigger movably mounted on the cradle;
   a pair of clamp arms resiliently mounted for movement on the cradle between an open position and a closed position;
   a latch device interconnecting the clamp arms and the trigger for retaining the clamp arms in the open position and for simultaneously releasing the clamp arms to the closed position in response to movement of the trigger relative to the cradle; and
   a base mounted on the cradle for calibrated adjustment of the cradle.

19. The gripping clamp as defined in claim 18 further comprising a guide extending between the cradle and the trigger for guiding movement of the trigger on the cradle.

20. The gripping clamp as defined in claim 19 wherein the trigger is resiliently engaged with the cradle for urging the trigger into engagement with the clamp arms.

21. A method of securing an alignment device on a patient's ankle comprising the steps of:
   movably mounting a triggering device on a cradle;

resiliently mounting a pair of clamp arms on the triggering device for movement between an open position and a closed position;

interconnecting the clamp arms and the cradle with a latch device for retaining the clamp arms in the open position and for simultaneously releasing the clamp arms to the closed position;

attaching the cradle to an extramedullary alignment device;

engaging the latch device for resiliently loading the clamp arms in the open position; and urging the cradle and the triggering device into engagement with the patient's ankle for automatically and simultaneously releasing the clamp arms to grip the patient's ankle.

* * * * *